(12) United States Patent
Choi

(10) Patent No.: US 9,433,470 B2
(45) Date of Patent: Sep. 6, 2016

(54) SURGICAL ROBOT SYSTEM AND METHOD FOR CONTROLLING SURGICAL ROBOT SYSTEM

(71) Applicant: Meere Company Inc., Gyeonggi-do (KR)

(72) Inventor: Seung Hee Choi, Gyeonggi-do (KR)

(73) Assignee: Meere Company Inc. (KR)

( * ) Notice: Subject to any disclaimer, the term of this patent is extended or adjusted under 35 U.S.C. 154(b) by 0 days.

(21) Appl. No.: 14/562,085

(22) Filed: Dec. 5, 2014

(65) Prior Publication Data

US 2015/0157411 A1 Jun. 11, 2015

(30) Foreign Application Priority Data

Dec. 9, 2013 (KR) ........................ 10-2013-0152632

(51) Int. Cl.
*B25J 13/00* (2006.01)
*A61B 19/00* (2006.01)

(52) U.S. Cl.
CPC ................................ *A61B 19/2203* (2013.01)

(58) Field of Classification Search
CPC .................. A61B 19/2203; A61B 2019/2223; A61B 2019/2238; A61B 2019/2234; A61B 19/56; A61B 19/22; B25J 9/1689; B25J 9/1664
USPC ......... 700/245, 257, 264; 318/568.11; 606/1
See application file for complete search history.

(56) References Cited

U.S. PATENT DOCUMENTS

| 2007/0093939 A1* | 4/2007 | Kobayashi | B25J 9/16 700/245 |
| 2007/0156285 A1* | 7/2007 | Sillman | A61B 19/22 700/245 |
| 2011/0105898 A1* | 5/2011 | Guthart | A61B 19/22 600/437 |
| 2014/0148818 A1* | 5/2014 | Komuro | A61B 18/1402 606/130 |

FOREIGN PATENT DOCUMENTS

| KR | 1020110118639 | | 10/2011 |
| KR | 1020120052573 | A | 5/2012 |
| KR | 1020120098342 | A | 9/2012 |
| KR | 1020120102453 | A | 9/2012 |

* cited by examiner

*Primary Examiner* — Dalena Tran
(74) *Attorney, Agent, or Firm* — Brinks Gilson & Lione

(57) ABSTRACT

A surgical robot system includes a slave robot, a master console, a first display and a control portion. The slave robot includes a plurality of robot arms at which surgical tools are mounted. The master console performs remote control on the slave robot in response to a manipulation of an operator. The first display is arranged around the slave robot. The control portion outputs image information displaying information about a position of the event on an image corresponding to a shape of the slave robot or the master console to the first display when the event occurs in the slave robot or the master console.

18 Claims, 11 Drawing Sheets

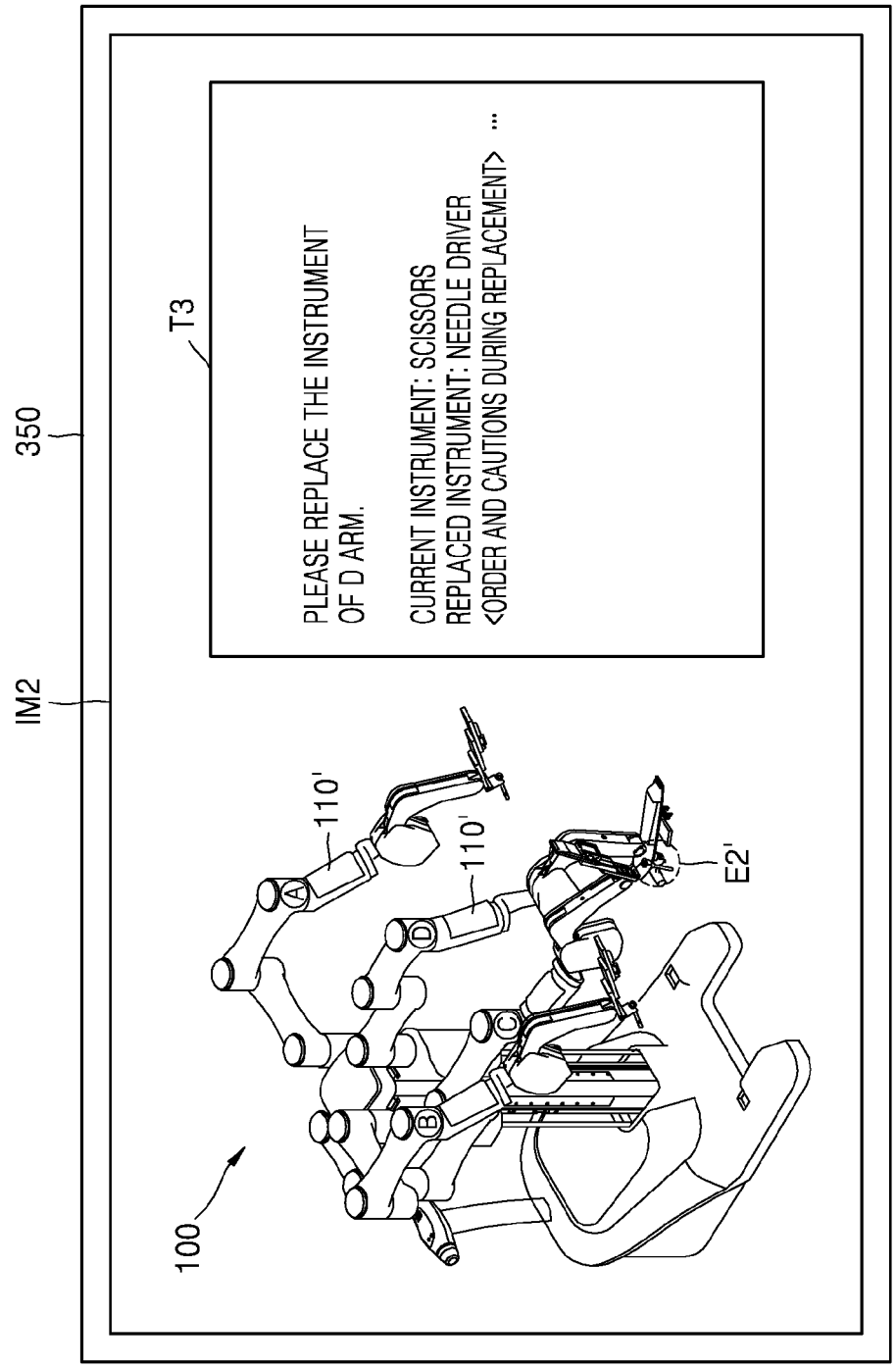

SURGICAL ROBOT SYSTEM AND METHOD FOR CONTROLLING SURGICAL ROBOT SYSTEM

PRIORITY

This application claims the benefit of Korean Patent Application No. 10-2013-0152632, filed on Dec. 9, 2013, in the Korean Intellectual Property Office, the disclosure of which is incorporated herein in its entirety by reference.

BACKGROUND OF THE INVENTION

1. Technical Field

One or more embodiments of the present inventive concept relate to a surgical robot system and a method for controlling the surgical robot system.

2. Background Art

Recently, robot systems for minimally invasive surgery including master consoles and slave robots have been introduced to and used in hospitals. An abnormal event or an unusual event may occur during the operation of a robot system for minimally invasive surgery. When such an event occurs, an immediate reaction thereto is urgently needed for safe surgery.

To meet the above requirement, the robot system for minimally invasive surgery is equipped with a light emitting device or a sound generating device operating when an abnormal event or an unusual event occurs so that the occurrence of an event may be immediately notified to an operator or assistant operator in an operating room When the occurrence of an event is notified to an operator or assistant operator in an operating room through light or sound, the operator or assistant operator may be immediately recognize the occurrence of an event. However, it is difficult to transmit detailed information such as a position where the event occurs or a type of the event. Also, since it is difficult to transmit information about what caused the event or what kind of action to take in response to the event. Accordingly, there is a limit in taking an immediate reaction to the occurrence of an event.

The above-described background technology is owned by the inventor to invent the present inventive concept or obtained in a process of inventing the present inventive concept and thus it cannot be said to be a well-known technology published to the public prior the filing of the present inventive concept.

SUMMARY OF THE INVENTION

One or more embodiments of the present inventive concept include a surgical robot system which may effectively respond to an event occurring during a robot surgery process by accurately and quickly transmitting information related to the event, including a position where the event occurs, to an operator or an assistant operator located nearby, and a method for controlling the surgical robot system.

Additional aspects will be set forth in part in the description which follows and, in part, will be apparent from the description, or may be learned by practice of the presented embodiments.

According to one or more embodiments of the present inventive concept, a surgical robot system includes a slave robot having a plurality of robot arms at which surgical tools are mounted, a master console performing remote control on the slave robot in response to a manipulation of an operator, a first display arranged around the slave robot, and a control portion outputting image information displaying information about a position of the event on an image corresponding to a shape of the slave robot or the master console to the first display when the event occurs in the slave robot or the master console.

The control portion may output text information related to the event to the first display with the image information.

The text information may include at least one of information about a type of the event, a cause of the event, a method for handling the event, or a combination thereof.

The event may include at least one of initialization of the slave robot or the master console, completion of preparation for an operation of the slave robot or the master console, a communication error between the slave robot and the master console, an error in an actuator of the slave robot, an error in a signal of a sensor provided in the slave robot, an error in power of the slave robot, an error in mounting of the surgical tools, a replacement of the surgical tools, reaching an operational limit of the slave robot or an operation of an electric surgical tool mounted on the slave robot, separation of a head of the operator from the master console, an input of a preset instruction by the operator, an input of a preset instruction by an assistant operator, generation of manipulation to move a position of the slave robot, or a combination thereof.

The surgical robot system may further include a second display that is arranged on the master console, and the second display may display image information corresponding to an image displayed on the first display.

The event may be generated according to an instruction of the operator, and the control portion may receive an input of the information about the position of the event from the operator.

The first display may be arranged on the master console, the event is generated according to an instruction of an assistant operator, and the control portion may receive an input of the information about the position of the event from the assistant operator and outputs the image information to the first display.

The control portion may further include a real-time robot image generation unit that generates in real time an image of the slave robot corresponding to a shape of the slave robot by using the information about the sensor of the slave robot.

According to one or more embodiments of the present inventive concept, a method for controlling a surgical robot system that includes a slave robot having a plurality of robot arms equipped with surgical tools, a master console performing remote control on the slave robot in response to a manipulation of an operator, and a first display arranged around the slave robot, includes generating an event in the slave robot or the master console, generating image information displaying information about a position of the event on an image corresponding to the slave robot or the master console, and outputting the image information to the first display.

The image information may further include text information related to the event.

The text information may include at least one of information about a type of the event, a cause of the event, a method for handling the event, or a combination thereof.

The event may include at least one of initialization of the slave robot or the master console, completion of preparation for an operation of the slave robot or the master console, a communication error between the slave robot and the master console, an error in an actuator of the slave robot, an error in a signal of a sensor provided in the slave robot, an error in power of the slave robot, an error in mounting of the surgical tools, a replacement of the surgical tools, reaching an operational limit of the slave robot or an operation of an electric surgical tool mounted on the slave robot, separation of a head of the operator from the master console, an input of a preset instruction by the operator, an input of a preset instruction by an assistant operator, generation of manipulation to move a position of the slave robot, or a combination thereof.

The surgical robot system may further include a second display that is arranged on the master console, and the second display may display image information corresponding to an image displayed on the first display.

The event may be generated according to an instruction of the operator, and the generating of the image information may further include receiving an input of the information about the position of the event from the operator.

The first display may be arranged on the master console, the event is generated according to an instruction of an assistant operator, and the generating of the image information may further include receiving an input of the information about the position of the event from the assistant operator.

The method may further include generating in real time an image of the slave robot corresponding to a shape of the slave robot by using the information about the sensor of the slave robot.

BRIEF DESCRIPTION OF THE DRAWINGS

These and/or other aspects will become apparent and more readily appreciated from the following description of the embodiments, taken in conjunction with the accompanying drawings in which:

FIG. 8 schematically illustrates an image displayed on a display of a vision cart according to the operation of an operator;

DETAILED DESCRIPTION OF THE INVENTION

Figure 1:
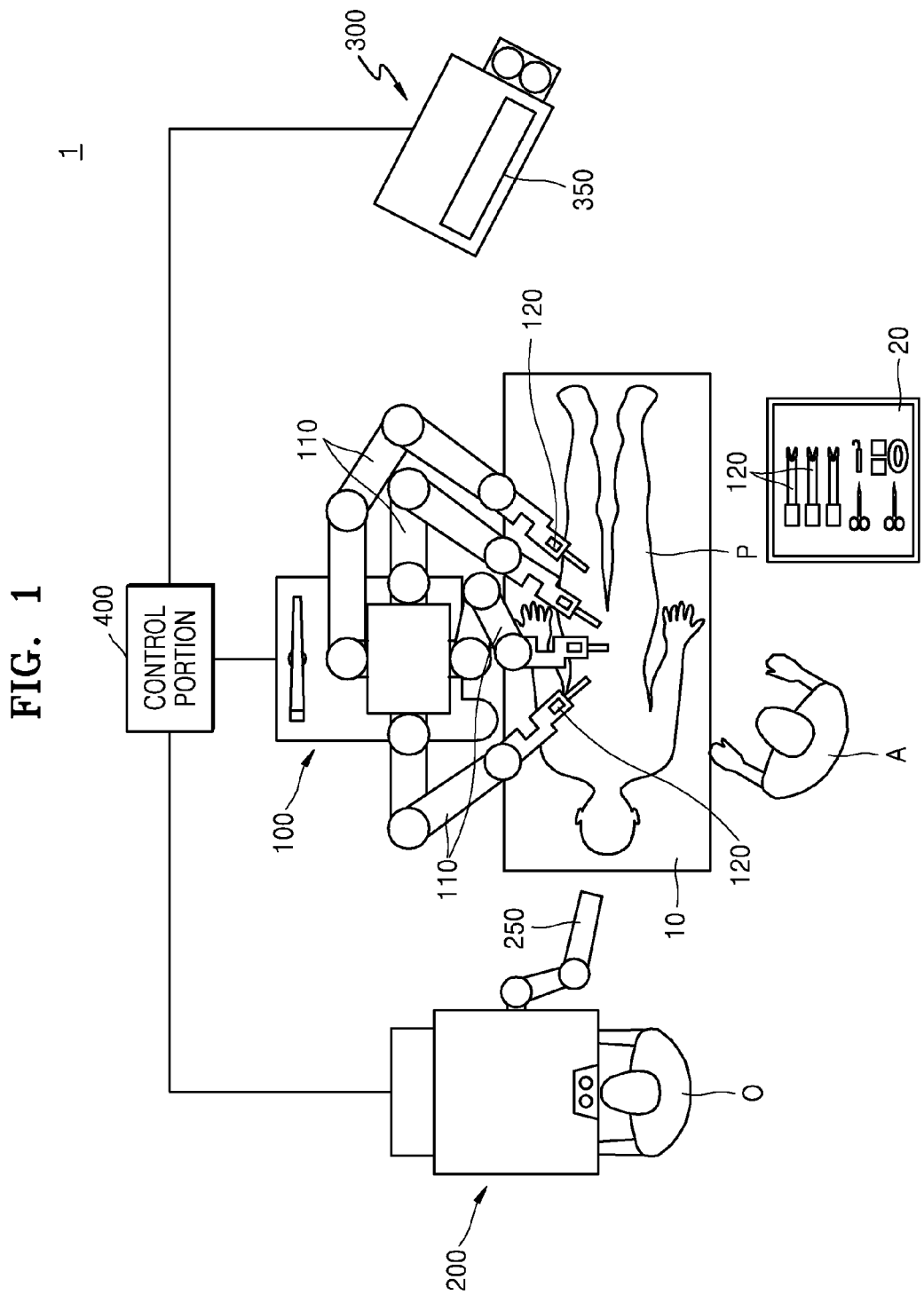
FIG. 1 is a plan view schematically illustrating a surgical robot system according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

FIG. 1 is a plan view schematically illustrates the structure of a surgical robot system 1 according to an embodiment.

Referring to FIG. 1, in an operating room, a patent P lies on an operating table 10, an operator O controls the surgical robot system 1, an assistant operator A assists in robot surgery at a side of a slave robot 100, and the surgical robot system 1 and a table 20 on which surgical tools 120 are placed are disposed around the operating table 10. The surgical robot system 1 according to the present embodiment performs minimally invasive surgery by using a robot according to a control of the operator O, and includes the slave robot 100, a master console 200, a vision cart 300, and a control portion 400.

The slave robot 100 includes a plurality of robot arms 110 and each of the robot arms 110 is provided with each of the surgical tools 120 or an endoscope. Each of the surgical tools 120 or the endoscope installed at each of the robot arms 110 is inserted into a body of the patient P placed on the operating table 10 so as to perform minimally invasive surgery. The operation and position of the surgical tool 120 inserted into the body of the patient P is controlled by the robot arms 110.

Figure 2:
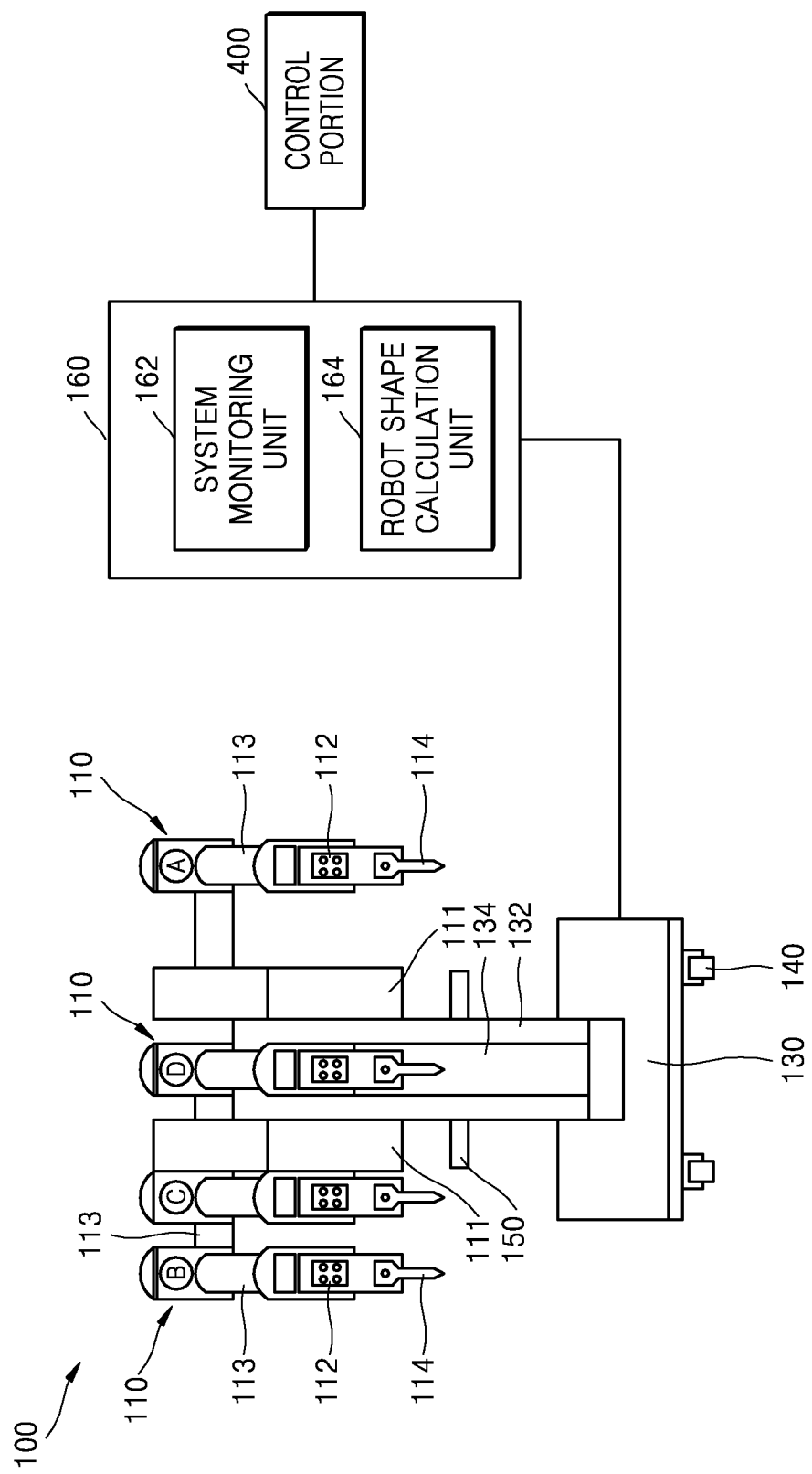
FIG. 2 schematically illustrates a slave robot of the surgical robot system of FIG. 1.

FIG. 2 schematically illustrates an example of the slave robot 100. Referring to FIG. 2, the slave robot 100 includes a base portion 130, a tower 132 installed on the base portion 130 to stand thereon, and the robot arms 110 arranged at the tower 132.

The base portion 130 includes a plurality of wheels 140 thereunder so that the slave robot 100 may move if necessary. At least some of the wheels 140 may receive a driving force from a motor (not shown). Also, a breaking system (not shown) for fixing the wheels 140 by preventing the slave robot 100 from moving during the minimally invasive surgery may be provided at the base portion 130. Also, a steering handle 150 for facilitating a change of a direction when the slave robot 100 is moving may be provided at the base portion 130.

The tower 132 supports the robot arms 110 and includes an elevation rail 134 for changing the position of the robot arms in a vertical direction. The elevation rail 134 may be equipped with a counter-weight mechanism (not shown) in order to offset the weight of the robot arms 110.

The robot arms 110 each includes a coupling portion 111 coupled to the elevation rail 134 of the tower 132, a robotic link including a plurality of joints and actuators, and a surgical tool mounting portion 112 for mounting one of the surgical tools 120. A motor (not shown) for elevating each of the robot arms 110 and a sensor (not shown) for measuring a vertical position of each of the robot arms 110, for example, a linear encoder, may be provided at the coupling portion 111 or the tower 132. The robotic link 113 may be provided with not only a motor for driving but also a sensor for measuring a driving amount, for example, an encoder for measuring a rotational angle of a joint. The surgical tool mounting portion 112 may be provided with a power transmitting portion for transmitting a driving force to the surgical tools 120 for the operation of the surgical tools 120. The surgical tool mounting portion 112 may include a holder 114 for holding a shaft body portion of each of the surgical tools 120. On the other hand, for identification of the robot arms 110, each of the robot arms 110 may be marked with an identification sign, for example, numbers or letters such as 1, 2, 3, 4, etc. or A, B, C, D, etc., or colors. Also, a light emitting device or a sound generating device for indicating a normal operation may be arranged at each of the robot arms 110.

The slave robot 100 may include a control unit 160 formed of an operating device including a microprocessor. The control unit 160 of the slave robot 100 may be directly installed on the slave robot 100 or may be disposed at a place remote from the slave robot 100 and electrically connected to the slave robot 100 via a wired/wireless manner. The control unit 160 of the slave robot 100 may include a system monitoring unit 162 for monitoring a state of the robot arms 110, a state of the surgical tools 120, and a communication state with the master console 200, and a robot shape calculation unit 164 for calculating a geometric shape of the slave robot 100 in real time by using kinematic information including a calculated value obtained from the sensor of the slave robot 100. The system monitoring unit 162 and the robot shape calculation unit 164 may be configured by hardware so as to be physically divided or by software that is not physically divided. The control unit 160 of the slave robot 100 is electrically connected to the control portion 400 of the entire surgical robot system 1 so as to interact with the master console 200 and the vision cart 300.

During the minimally invasive surgery, the slave robot 100 is covered with drapes (not shown) to be isolated from a sterilized environment in the operating room. However, the surgical tools 120 that are inserted into the body of the patient P are at least partially located in the sterilized environment. An interface adaptor (not shown) for electrical/mechanical coupling between the robot arms 110 inside the drapes and the surgical tools 120 outside the drapes may be provided inside the drapes.

Figure 3:
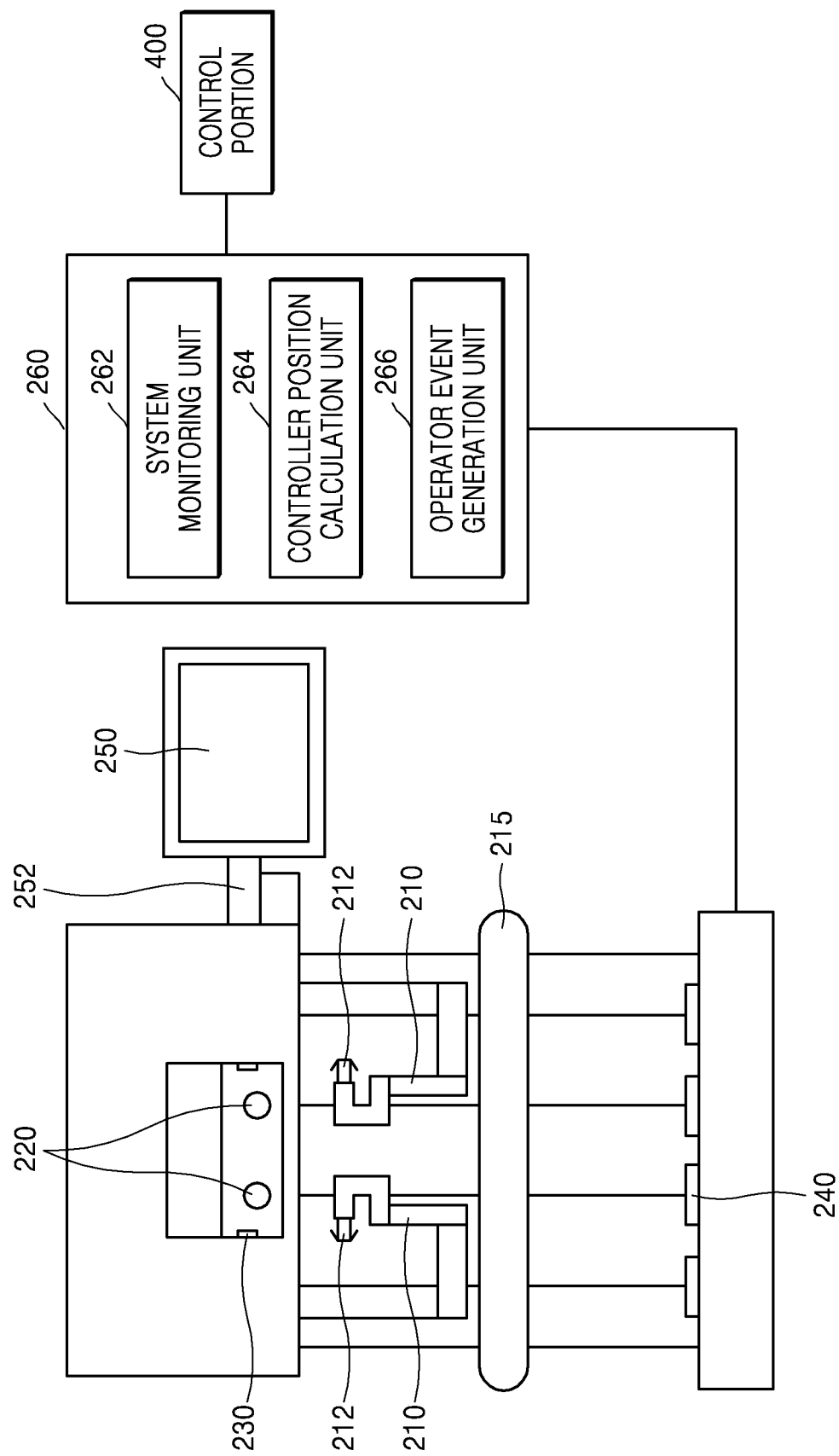
FIG. 3 schematically illustrates a master console of the surgical robot system of FIG. 1.

The master console 200 generates a control signal to control the slave robot 100 according to a manipulation by the operator O. FIG. 3 schematically illustrates the master console 200. Referring to FIG. 3, the master console 200 includes an endoscopic image display 220 to display an image captured by the endoscope installed on the robot arms 110 of the slave robot 100 to the operator O, a hand controller 210, a foot pedal 240, an auxiliary display 250, a head sensor 230, and a controller 260 of the master console 200. The master console 200 is generally arranged in the operating room with the slave robot 100. However, the present embodiment is not limited thereto and the master console 200 may be provided outside the operating room, as occasion arises. Furthermore, the master console 200 may be located outside a hospital where minimally invasive surgery is performed, so as to be used to perform a remote operation at a place located far from the hospital. Also, the master console 200 may be provided in a multiple number inside the operating room. When the surgical robot system 1 includes a plurality of master consoles, a plurality of operators who control the master consoles may perform separate roles during a robot surgery.

The endoscopic image display 220 is to transmit left-eye and right-eye images obtained from a stereo endoscope installed on the slave robot 100 to the operator O. The endoscopic image display 220 includes a pair of eye-contact displays respectively displaying the left-eye and right-eye images. Although in the present embodiment the endoscopic image display 220 is described to be formed of an eye-contact type, the endoscopic image display 220 may be configured to be a well-known non-eye-contact stereo vision display.

The hand controller 210 controls the slave robot 100 according to hand actions of the operator O. The hand controller 210 includes a link formed of a plurality of joints and a sensor such as an encoder is provided at each joint to measure a movement of the joint. Also, the hand controller 210 may include a grip controller 212 to control an operation of an end effector (not shown) of each of the surgical tools 120. Also, an actuator to restrict an operation range of the operator O or perform force feedback to the operator O may be provided in the hand controller 210.

On the other hand, the master console 200 may be provided with an arm rest 215 to allow the operator O to conveniently control the hand controller 210. The arm rest 215 may be provided with a touch screen (not shown) for providing a user interface to allow the operator O to obtain or control information about the surgical robot system 1.

The foot pedal 240 provides an additional control method in addition to the hand controller 210 manipulated by the operator O. The foot pedal 240 may be provided in a lower portion of the master console 200 in a multiple number so that the operator O may control the slave robot 100 by using his/her feet. Each foot pedal 240 may be set to control various functions such as turning a clutch mode on/off or actuating an electric surgical tool.

The auxiliary display 250 may display an endoscopic image or an image showing a state of the surgical robot system 1 so that other persons may see the same screen that the operator O sees. The auxiliary display 250 is supported by a support arm 252 that is configured to include joints so that the operator O may freely move the auxiliary display 250 to a desired position. Also, the auxiliary display 250 may be configured in the form of a touch screen to receive an input by the operator O.

The head sensor 230 monitors a position of the head of the operator O. When the operator O sets his/her head off from the endoscopic image display 220, the head sensor 230 may sense such a movement. The head sensor 230 may be formed of a proximity sensor that senses the presence of a nearby object.

The controller 260 of the master console 200 controls the master console 200 and transmits a manipulation signal of the hand controller 210 and the foot pedal 240 of the master console 200 to the control portion 400 of the surgical robot system 1 so that the slave robot 100 may operate in engagement thereto. The controller 260 of the master console 200 may be configured with a microprocessor and may include a system monitoring unit 262, a controller position calculation unit 264, and an operator event generation unit 266. The system monitoring unit 262, the controller position calculation unit 264, and the operator event generation unit 266 may be configured in the form of being divided by hardware or may be configured by software in the form of not being physically divided.

The system monitoring unit 262 is a portion for detecting various events occurring in the master console 200 and detects a situation in which, for example, an error generated in the master console 200, the operator O sets his/her head off from the endoscopic image display 220, or the operator O makes a touch input to the auxiliary display 250. When occurrence of an event in the system monitoring unit 262 is detected, the occurrence of an event is transmitted to the control portion 400 of the surgical robot system 1.

The controller position calculation unit 264 calculates a shape of the hand controller 210 in real time by using measured values of the sensors of the hand controller 210 and accordingly transmits a control signal of the slave robot 100 to the control portion 400 of the surgical robot system 1. Also, when the position of the hand controller 210 approaches a set movement range to prevent the surgical tools 120 mounted in the slave robot 100 from operating in an excessive range, the controller position calculation unit 264 may operate a driving portion of the hand controller 210 to restrict a movement of the hand controller 210 or perform a feedback in a method for resisting the movement of the hand controller 210.

When the surgical robot system 1 needs to be controlled because the operator O has an instruction or a message to an assistant operator A besides a situation where, for example, an error occurs in the master console 200, the operator event generation unit 266 may transmit a command that the operator O inputs to the master console 200, to the control portion 400 of the surgical robot system 1. The input of a control command by the operator O may be performed in a touch manner through a graphic user interface provided in the auxiliary display 250. In other words, when the operator O performs a touch operation on the auxiliary display 250, the operator event generation unit 266 may transmit information about the event to the control portion 400 of the surgical robot system 1.

Figure 4:
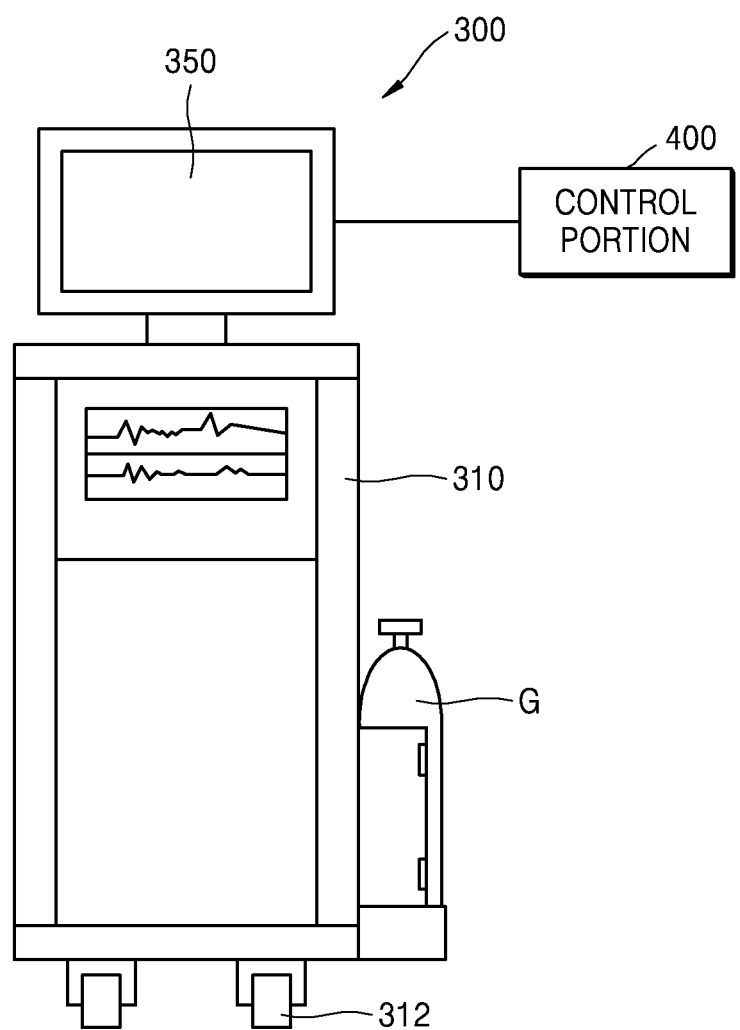
FIG. 4 schematically illustrates a vision cart of the surgical robot system of FIG. 1.

The vision cart 300 may include a display 350 to transmit information needed for surgery to personnel, for example, the assistant operator A, in the operating room. FIG. 4 schematically illustrates the vision cart 300. Referring to FIG. 4, the vision cart 300 may further include, in addition to the display 350, a gas container G containing a gas needed for surgery, an apparatus displaying a state of the patient P, and a frame 310 supporting the gas container G and the apparatus. Also, the vision cart 300 may further include a wheel 312 to facilitate a movement of the vision cart 300. In the present embodiment, in particular, when an event occurs, the vision cart 300 may transmit the occurrence of an event to the assistant operator A. In detail, the vision cart 300 may display a type of the event, a position where the event occurs, a cause of the occurrence of the event, and an event process method, to the assistant operator A. To this end, when an event occurs in the slave robot 100 or the master console 200, the control portion 400 of the surgical robot system 1 transmits image information corresponding to the occurrence of an event to the display 350 to be display thereon.

Figure 5:
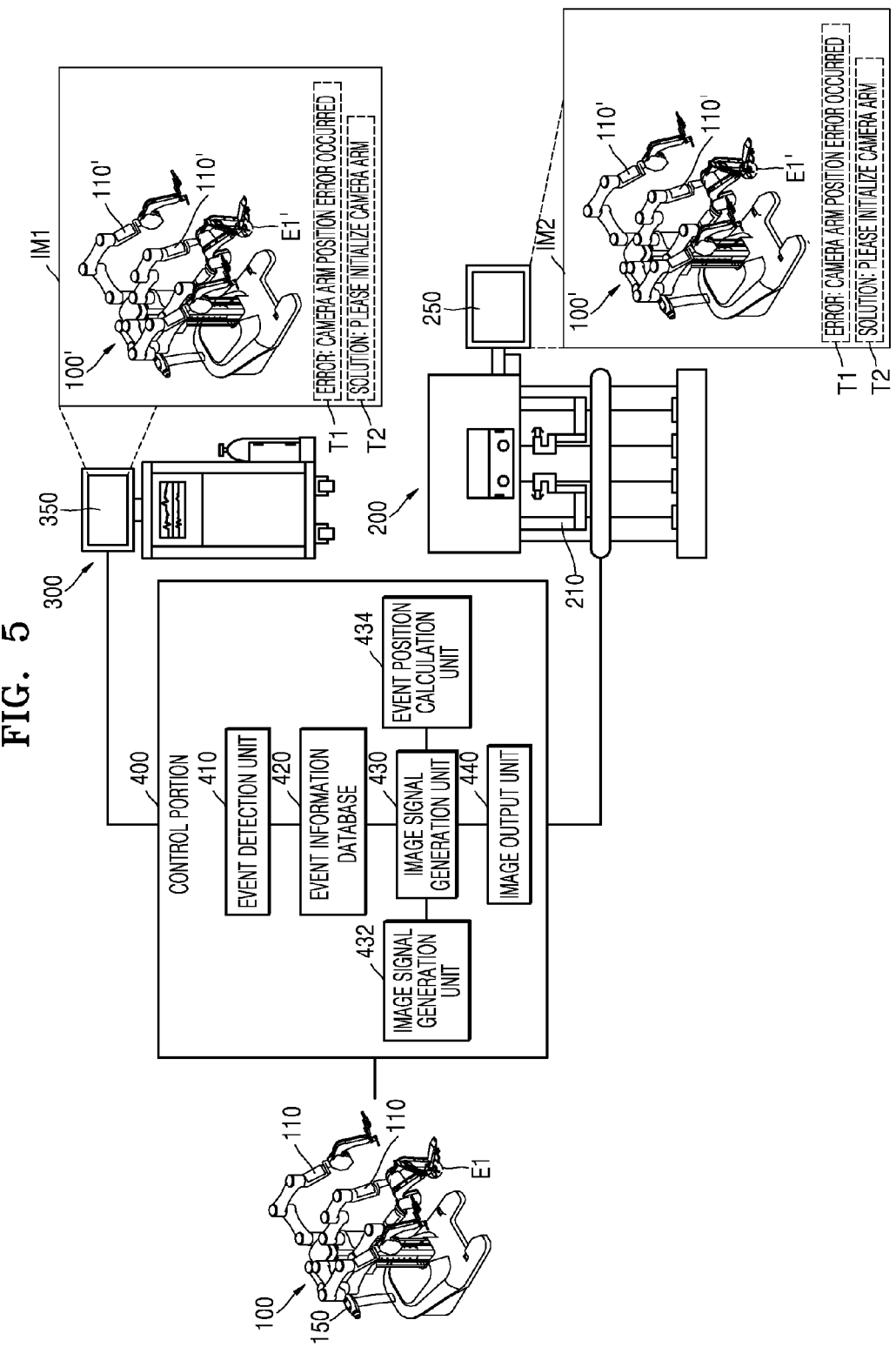
FIG. 5 schematically illustrates an operation of the surgical robot system of FIG. 1.

FIG. 5 schematically illustrates a process in which the control portion 400 of the surgical robot system 1 processes an event that occurs in the slave robot 100.

As illustrated in FIG. 5, when an event, for example, a positional error, occurs in one of the robot arms 110 of the slave robot 100, which is equipped with an endoscope, the control portion 400 of the surgical robot system 1 detects the occurrence of the event and then the event is processed in a method for controlling the vision cart 300 and the master console 200 according thereto.

To perform the function, the control portion 400 of the surgical robot system 1 may include an event detection unit 410, an event information database 420, an image signal generation unit 430, and an image output unit 440.

The event detection unit 410 detects occurrence of an event in the surgical robot system 1 including the slave robot 100, the master console 200, and the vision cart 300 and initiates an event processing procedure. To detect the occurrence of an event, the event detection unit 410 may be configured to receive an event occurrence signal from the control unit 160 of the slave robot 100 or the controller 260 of the master console 200, or acquire a sensor signal directly from the slave robot 100 or the master console 200.

The event information database 420 stores information about a processing method according to the type of an event, the cause of the occurrence of an event, and the form of an event, and outputs appropriate information in response to the occurrence of an event. In the present embodiment, when an error occurs in a mark E1 indicating a portion of the robot arms 110 equipped with an endoscope, the event information database 420 outputs information about a method for handling the event.

The image signal generation unit 430 generates image information indicating a position where the event occurs, with an image corresponding to the slave robot 100 or the master console 200. As in the present embodiment, when an error occurs in the robot arm 110 equipped with an endoscope of the slave robot 100, the image signal generation unit 430 generates image information including an image 100' of the slave robot 100 and a mark E1' indicating a robot arm 110' where the error occurs. The mark E1' indicating the robot arm 110' where the error occurs may be configured in the form of a color, an index line, a figure, a blinker, etc. so as to be distinguished from a surrounding image.

The image 100' of the slave robot 100 may be an image that varies in real time corresponding to a change in the shape of the slave robot 100 as the slave robot 100 operates. To this end, the control portion 400 may include a real-time robot image generation unit 432 that reconfigures in real time a current shape of the slave robot 100 by using a signal of the sensor of the slave robot 100. Also, the control portion 400 may further include an event position calculation unit 434 that reflects a change in the position of the mark E1 because the mark E1 indicating the position where the event occurs is changed to the mark E1' in each of output images IM1 and IM2 as the image 100' of the slave robot 100 changes in real time.

The image signal generation unit 430 may add the information obtained from the event information database 420 with the image of the slave robot 100 or the master console 200, to the output images IM1 and IM2. In other words, when an error occurs in the robot arm 110 equipped with an endoscope of the slave robot 100, text information T1 indicating that the error occurs and text information T2 about a method for handling the error may be synthesized in the image of the slave robot 100 or the master console 200.

Also, the image signal generation unit 430 may generate an image indicating an event occurrence position on an image obtained by enlarging the entire or a part of the surgical robot system 1 according to the type of an event. For example, when an error occurs in a communication line between the slave robot 100 and the master console 200, the image signal generation unit 430 may generate an image showing a mark indicating the communication line therebetween with an image showing the slave robot 100 and the master console 200, and may display together text information indicating that an error occurs in the communication line and text information about a method for solving the error. On the other hand, when an error occurs in a small area such as the surgical tools 120, to more clearly indicate a position where the error occurs, the image signal generation unit 430 may indicate the position where the error occurs on an image obtained by enlarging a portion of the surgical tools 120 of the slave robot 100, or may generate an image signal simultaneously showing an image of the whole of the slave robot 100 and the enlarged image of the error occurrence position of the surgical tools 120. In this case, the text information including a description of the error and a method for handling the error may be included in the image.

The image output unit 440 outputs the image signal generated by the image signal generation unit 430 to the auxiliary display 250 of the master console 200 or the display 350 of the vision cart 300. The image output unit 440 may output the image to both of the auxiliary display 250 of the master console 200 and the display 350 of the vision cart 300, or to any one thereof, according to the type of an event. When the image output unit 440 simultaneously outputs the image to both of the auxiliary display 250 of the master console 200 and the display 350 of the vision cart 300, the output image may be the same image or images corresponding to each other.

As described above, when an event occurs in a portion of the slave robot 100, for example, when an error occurs in the robot arm 110 equipped with an endoscope, the image 100' of the slave robot 100 with the mark E1' indicting the error occurrence position is displayed on the display 350 of the vision cart 300 and the auxiliary display 250 of the master console 200, and the text information T1 about the occurrence of the event and the text information T2 about the handling method are displayed together. Accordingly, the operator or the assistant operator A in the operating room may easily recognize the position where an error occurs and may immediately recognize the method for handling the error.

In particular, when an error occurs in the slave robot 100 having a complicated mechanical structure, it is difficult to identify, or often confuse, the position of the error and further it is very difficult to see what action should be taken when an error occurs. The surgical robot system 1 according to the present embodiment may effectively solve the above difficulties. When an even such as the error in the surgical robot system 1 occurs during surgery, if the position where the event occurs or the method for handling the event is not identified and thus a proper processing procedure is disregarded, the life of the patient P may be endangered. In this case, the surgical robot system 1 of the present embodiment may effectively remove potentially dangerous elements in the robot surgery and thus possibility of medical accidents may be greatly reduced.

Also, since the surgical robot system 1 of the present embodiment reflects every moment a change in the geometric shape of the surgical robot system 1 during operation by forming in real time an image corresponding the surgical robot system 1, in particular, the slave robot 100 or the master console 200, to be displayed on the display 350 of the vision cart 300. Accordingly, the personnel in the operating room may more intuitively and more quickly identify the position where an event occurs.

On the other hand, when an event occurs in the surgical robot system 1 and occurrence of the event is displayed on the display 350 of the vision cart 300, light emission or sound may be generated together in order to draw attention of the operator O or the assistant operator A. To this end, a light emitting device or a speaker may be provided in the surgical robot system 1.

In the above-description, although the occurrence of an error in the robot arms 110 of the slave robot 100 is described as an example of an event that may occur in the surgical robot system 1, the event that may occur in the surgical robot system 1 may be an event related to a state of the surgical robot system 1, for example, initialization of the surgical robot system 1 such as checking whether the slave robot 100 is initialized or checking whether the master console 200 is initialized, notifying completion of preparation for the operation of the surgical robot system 1, notifying occurrence of a communication error in various motors and power controllers, malfunction of a servo motor, read failure of values of various sensors including en encoder, generation of an error in power such as deficiency in a battery amount or generation of an overcurrent, excessive frequency of use of the surgical tools 120, defective installation of the surgical tools 120, loss of a control signal or image data, etc. Also when the operation of the slave robot 100 needs to be temporarily stopped in a case, for example, the operator O sets his/her head off from the endoscopic image display 220 to see other things, the situation may be recognized as an event. Also, when a current is applied to an electrocautery, the slave robot 100 reaches a limit position of the operation, the robot arms 110 may collide against one another, the steering handle 150 is manipulated during the operation of the slave robot 100, etc., the above cases may be recognized as events and displayed on the auxiliary display 250 of the master console 200 or the display 350 of the vision cart 300. Also, when the operator O needs to transmit a message to the assistant operator A, for example, the surgical tools 120 need to be replaced or an endoscope needs to be cleaned, the operator O may directly generate an event so as to display the message on the display 350 of the vision cart 300. Also, when a plurality of master consoles are connected to the surgical robot system 1, only some of the robot arms 110 are operated, unintended positional movements of the robot arms 110 occur, etc., the surgical robot system 1 of the present embodiment recognize the above situations as events and may display an image indicating the position where the event occurs and a method for handling the event on the display 350 of the vision cart 300 or the auxiliary display 250 of the master console 200.

Next, a method for controlling a surgical robot system according to another embodiment is described. To describe the method for controlling a surgical robot system of the present embodiment in an easier way, the method for controlling a surgical robot system of the present embodiment is applied to the above-described surgical robot system 1.

Figure 6:
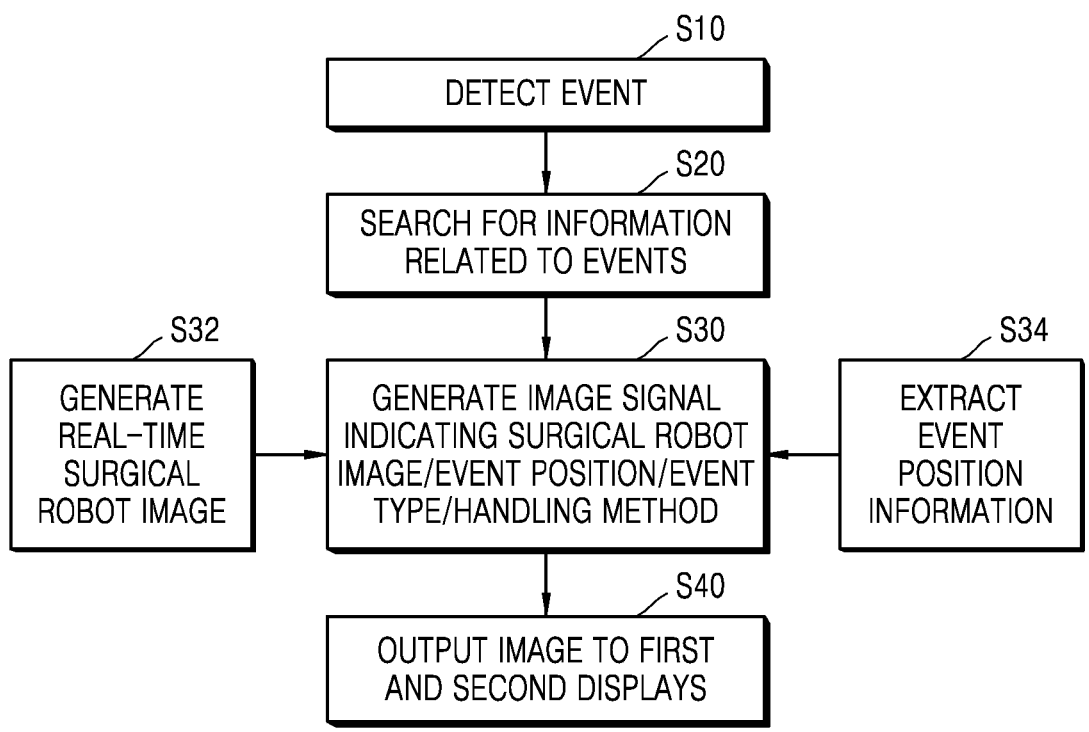
FIG. 6 is a flowchart for schematically describing a method for controlling a surgical robot system according to another embodiment.

FIG. 6 is a flowchart for schematically describing a method for controlling a surgical robot system according to another embodiment. Referring to FIG. 6, the method for controlling a surgical robot system of the present embodiment includes detecting an event (S10), searching for information related to events (S20), generating an image signal (S30), and outputting an image to a display (S40).

In the detecting of an event (S10), the control portion 400 of the surgical robot system 1 detects occurrence of an event. An event that may occur in the surgical robot system 1 may include occurrence of an error or interrupt in the surgical robot system 1, an input of a control command by the operator O when the operator O intends to give an order to the assistant operator A, etc.

In the searching of information related to events (S20), database DB storing information related to events is searched for to read out information corresponding to the event, for example, a cause of the occurrence of the event and a method for handling the event.

In the generating of an image signal (S30), an image is generated by synthesizing an image showing the whole or a part of the surgical robot system 1 and an image showing the position where the event occurs, and data obtained by searching for the inventive concept related to events. For example, an image signal generated in the present operation may be an image signal in which the mark E1' indicating the position where an error occurs is added to the image 100' corresponding to the surgical robot system 1 and the text information T1 about the type of an error and the text information T2 about the method for handling the error are displayed together. Also, the image generated in the present operation may be an image in which the position of an event is indicated on a real-time image of the surgical robot system 1, in particular, the slave robot 100. To this end, the method for controlling a surgical robot system of the present embodiment may further include calculating a geometric shape of the surgical robot system in real time by using sensor information of the surgical robot system (S32), and reading out the position where an event occurs to synthesize the event occurrence position on a real-time image of the surgical robot system (S34).

In the outputting of an image to a display (S40), the images IM1 and IM2 including the image 100' of the surgical robot system showing the mark E1' indicating the event occurrence position and the text information T1 and T2 related to the event related to the event are displayed on the display 350 of the vision cart 300 or the auxiliary display 250 of the master console 200 which is provided in the surgical robot system. As such, when an image is output to the displays 250 and 350, the operator O and the assistant operator A in the operating room may easily recognize the type of the event, the cause of the occurrence of the event, and the handling method thereof so as to quickly respond to the event, thereby danger of a medical accident may be effectively reduced.

As described above, among the above events, in addition to the case in which the surgical robot system generates an event or interrupt by itself, there is a case in which the operator O intentionally generates an event. The following description described the case in detail.

Figure 7A:
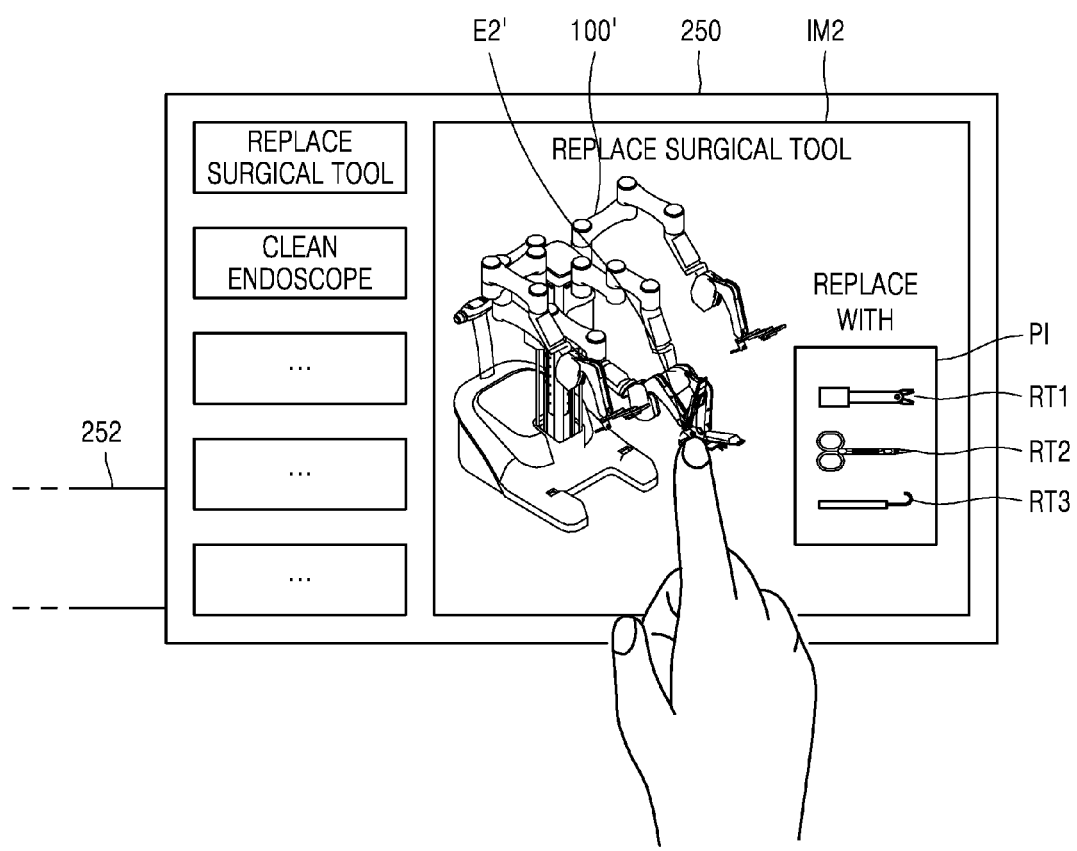
FIGS. 7A and 7B schematically illustrate that an operator operates a display.
Figure 7B:
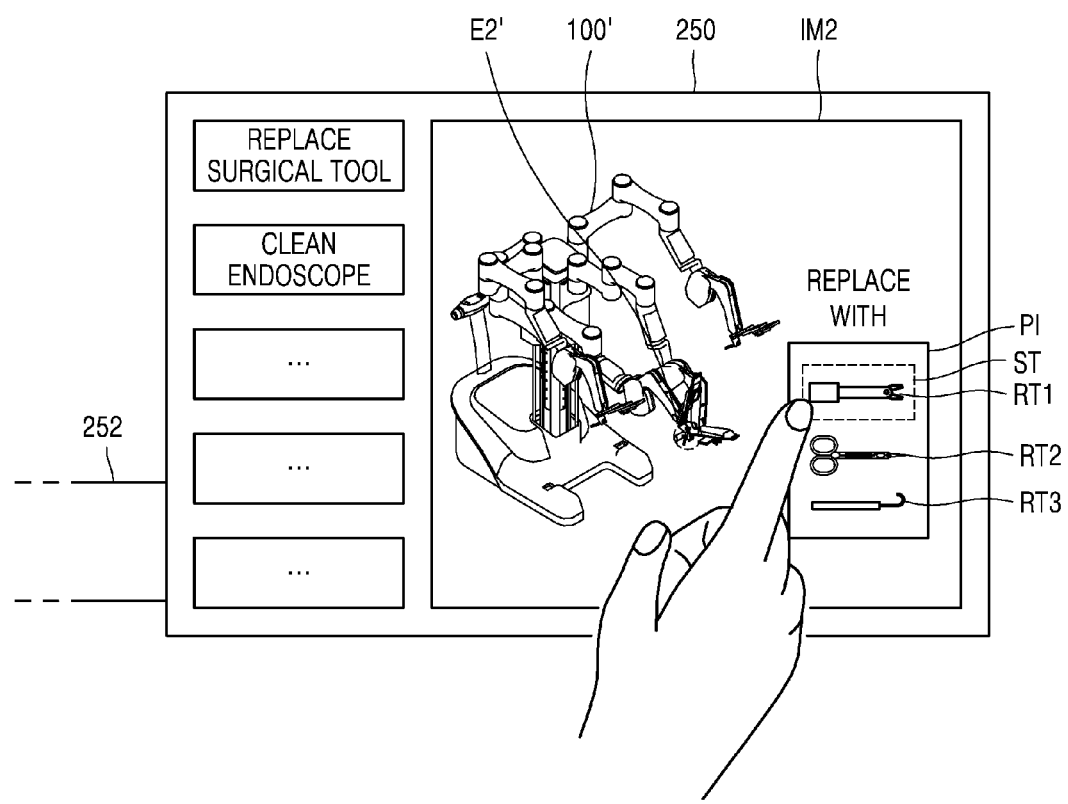

FIGS. 7A and 7B schematically illustrate that the operator O generates an event by manipulating the auxiliary display 250 of the master console 200. FIG. 8 schematically illustrates the image IM1 displayed on the display 350 of the vision cart 300 according to the occurrence of the event. In FIGS. 7A, 7B, and 8, a case of instructing replacement of the surgical tools 120 is described as one example of the events generated by the operator O.

As illustrated in FIG. 7A, when the operator O determines that the surgical tool 120 mounted on the slave robot 100 needs to be replaced with another surgical tool 120, the operator O may select a surgical tool replacement menu displayed on the auxiliary display 250 of the master console 200 and then select a surgical tool to be replaced by touching the surgical tool displayed on the auxiliary display 250. Then, a mark E2' indicating the position of the surgical tool to be replaced is displayed. Also, the controller 260 of the master console 200 may display a list PI of replaceable surgical tools RT1, RT2, and RT3 on the image IM2. On the other hand, prior to the above process, the operator O probably sets eyes off from the endoscopic image display 220 by lifting his/her head, and thus, the control portion 400 of the surgical robot system 1 may detect an event that the operator O sets his/her head off and may first display the event on the display 350 of the vision cart 300.

Referring to FIG. 7B, when the replaceable surgical tools RT1, RT2, and RT3 are displayed on a screen, the operator O may touch and select one of the replaceable surgical tools RT1, RT2, and RT3. When a new surgical tool is selected, a mark ST is displayed for the operator O to recognize the selected surgical tool RT1. Also, a message asking whether selection is completed may be displayed on the screen.

As such, when the selection of a replaceable surgical tool and a new surgical tool is completed, the control portion 400 of the surgical robot system 1 detects the selection as an event and performs a procedure corresponding thereto. In other words, the control portion 400 of the surgical robot system 1 generates the image IM2 displaying an image of the surgical robot system, the position of an event, and a method for handling an event, and outputs the same to the display 350 of the vision cart 300. Accordingly, as illustrated in FIG. 8, the mark E2' indicating the position of the surgical tool to be replaced is displayed with the image 100' of the slave robot 100 on the display 350 of the vision cart 300, and an instruction of the operator O to replace what surgical tool with what surgical tool and text information T3 that guides the procedure during replacement are displayed.

As such, when the instruction of the operator O are processed, the assistant operator A may clearly recognize the instruction of the operator O and thus efficiency of communication is greatly improved compared to a method for the related art in which the operator O give an instruction with voice. Accordingly, a delay in surgery or generation of a medical accident due to wrong replacement of a surgical tool by the assistant operator A may be effectively reduced.

Although in the above description the instruction to replace the surgical tool 120 is described as an example of an event according to the instruction of the operator O, an instruction of cleaning an endoscope, a passive alignment of the robot arms 110, an instruction related to other surgery, etc. may be processed by the above-described method.

Figure 9:
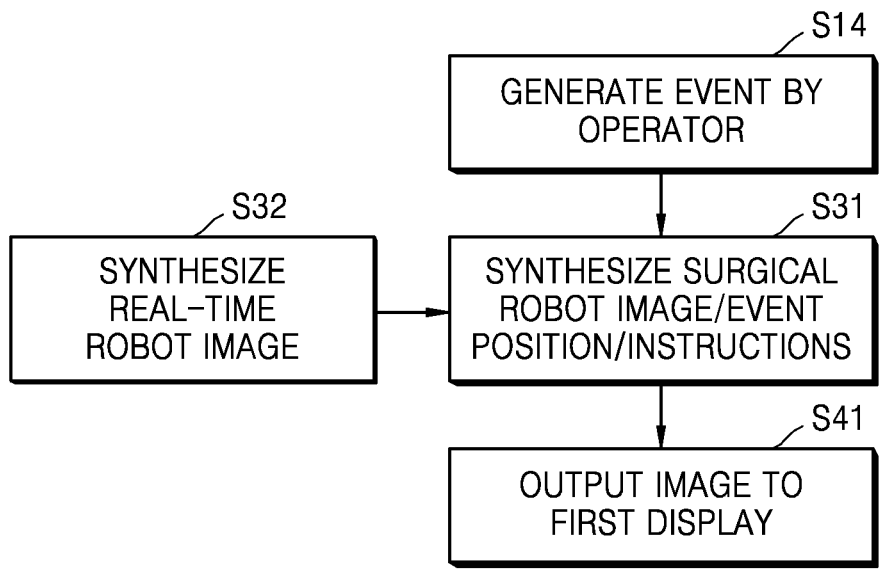
FIG. 9 is a flowchart for schematically describing a method for controlling a surgical robot system according to manipulation by an operator.

FIG. 9 is a flowchart for schematically describing a process of processing an event according to manipulation by the operator O. As described above, when the operator O manipulates the master console 200 to generate an event (S14), the surgical robot system 1 recognizes the event and generates an image showing the image 100' of the surgical robot system 1, the mark E2' indicating the position of the event, and the text information T3 about the instruction (S31). The image 100' of the whole or a part of the surgical robot system 1 may be a real-time image reflecting a current state of the surgical robot system 1 (S32). The generated image is output through the display 350 of the vision cart 300 so as to be seen by the assistant operator A (S41).

Figure 10:
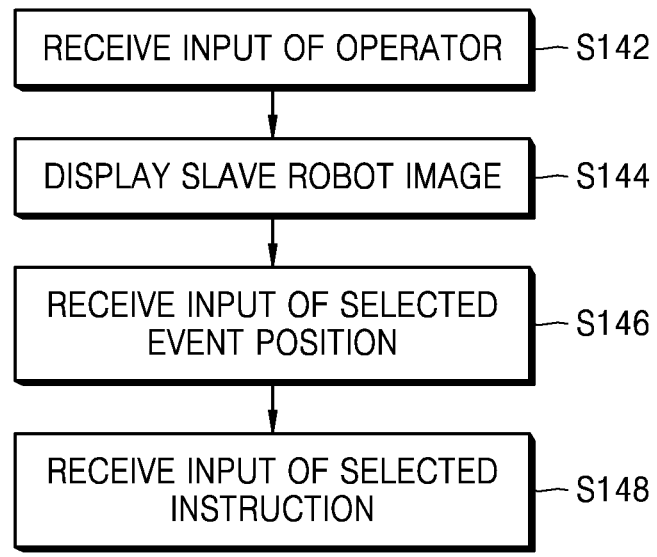
FIG. 10 is a flowchart for schematically describing a process in which an operator generates an event.

In detail, the process in which the operator O generates an event may include, as illustrated in FIG. 10, receiving an input of the operator O, which is performed by the master console 200 (S142), displaying a part or the whole of the surgical robot system 1 (S144), receiving a position of an event selected by the operator O (S146), receiving an instruction or a message selected by the operator O (S148).

In the receiving of an input of the operator O which is performed by the master console 200 (S142), a menu displayed on the auxiliary display 250 of the master console 200, for example, an instruction to replace a surgical tool, an instruction to clean an endoscope, etc., and selected by the operator O, is detected.

The displaying of the surgical robot system 1 (S144) is an operation of displaying the whole or a part of the surgical robot system 1 on the auxiliary display 250 of the master console 200. Since the surgical robot system 1 is displayed in a graphical image, the operator O may intuitively and easily select a portion to be worked by the assistant operator A.

In the receiving of a position of the event selected by the operator O (S146), the controller 260 of the master console 200 detects a position of the event selected by the operator O in a method such as screen touch. When the operator O selects the position of an event, the controller 260 may display a selection menu including various instructions or messages on the image IM1. Accordingly, the operator O may select a desired menu and the controller 260 may detect the selection and obtain detailed information about the event by the operator O (S148).

As such, when the controller 260 of the master console 200 detects the event generated by the operator O, the detection of the event is transmitted to the control portion 400 of the surgical robot system 1, and the image and information corresponding to the display 350 of the vision cart 300 are displayed so that the intension of the operator O may be clearly and visually transmitted to other personnel in operating room.

On the other hand, although in the above-description the surgical robot system 1 generates an event by itself according to a state of the surgical robot system 1 or an event is generated according to the instruction of the operator O, the event may be generated by manipulation of the assistant operator A. For example, when the assistant operator A finds an error that is not detected by the surgical robot system 1 during robot surgery or the assistant operator A has a message to transmit to the operator O, the assistant operator A may generate an event to the surgical robot system 1.

Figure 11:
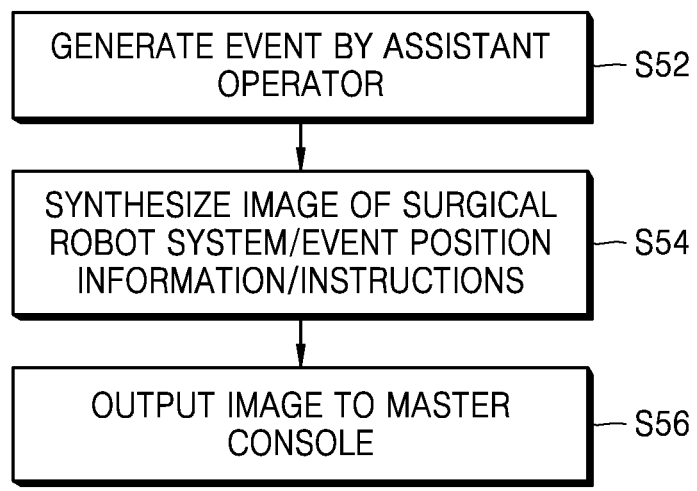
FIG. 11 is a flowchart for schematically describing a process in which an assistant operator processes an event.

FIG. 11 is a flowchart for schematically describing a process of handling an event when the assistant operator A generates the event. Referring to FIG. 11, a process of handling an event input by the assistant operator A includes generating an event, which is performed by the assistant operator A (S52), generating visual information including an image of the surgical robot system 1 and information related to the event (S54), and outputting the visual information as an image in the master console 200 (S56).

In the generating of an event by the assistant operator A, the assistant operator A generates an event in the surgical robot system 1 by performing a preset action such as touching the display 350 of the vision cart 300 or manipulating an emergency stop button. When the assistant operator A generates an event, the control portion 400 monitors and processes the generation of an event. In detail, the control portion 400 may display the image of the surgical robot system 1 including the slave robot 100 and the master console 200 on the display 350 of the vision cart 300, and may provide the assistant operator A with a graphic user interface for inputting event related information such as a position of the event, a type of the event, an instruction, etc. Accordingly, the assistant operator A may input event position information by touching a position of the event on the image of the surgical robot system 1 that is displayed on the display 350 of the vision cart 300, and may also input a type of the event, a cause of the event, a handling method, etc.

In the generating of visual information including an image of the surgical robot system 1 and information related to the event (S54), the control portion 400 synthesizes image information including the event related information such as the event position information and an instruction with an image of the whole or a part of the surgical robot system 1 including the slave robot 100 or the master console 200, by using the information about the event generated by the assistant operator A.

In the outputting of an image to the master console 200 (S56), the image information generated by the control portion 400 is output to the endoscopic image display 220 or the auxiliary display 250 of the master console 200. Accordingly, the operator O may visually recognize the information related to the event generated by the assistant operator A. On the other hand, the control portion 400 may output an image corresponding to the image output to the master console 200 also to the display 350 of the vision cart 300.

As such, the event by the assistant operator A and the event related information such as a position of the event, a message, etc. are visually transmitted to the operator O and thus the communication between the assistant operator A and the operator O may be performed very quickly and accurately.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present inventive concept have been described with reference to the figures, it will be understood by those of ordinary skill in the art that various changes in form and details may be made therein without departing from the spirit and scope of the present inventive concept as defined by the following claims.

For example, although in the above-described embodiment the display 350 is described to be arranged in the vision cart 300, the display for displaying an image about an event may be installed at any position where the assistant operator A sees well, such as, at other positions in the operating room, not at the vision cart 300, for example, on a well, a ceiling, or the master console 200.

Also, although in the above-described embodiment, the master console 200 does not separately include the endoscopic image display 220 and the auxiliary display 250, the master console 200, without having a separate auxiliary display, may display the event related image on an endoscopic image of the endoscopic image display 220 in the form of a picture-in-picture image or a pop-up image.

Also, although in the above-described embodiment, the generation of an event by the operator O and the information about the event are described to be input by the operator O through the auxiliary display 250 of the master console 200, the generation of an event by the operator O and the information about the event may be input through a touch panel separately provided on the arm rest 215 of the master console 200, or through the hand controller 210.

Also, if the function of generating an event by the operator O is not necessary or the input of an event generated by the operator O is not performed through the auxiliary display 250, the master console 200 may not include the auxiliary display 250.

Also, although in the above-identified embodiment, the image of the surgical robot system showing the position of an event, in particular, the image 100' of the slave robot 100 is described to be a real-time image, the image of the surgical robot system 1 showing the marks E1' and E2' indicating the positions of the event may be a fixed image obtained by simplifying the surgical robot system 1.

Also, although in the above-described embodiment, the surgical robot system 1 is described to be used for performing a minimally invasive surgery on a human body, the surgical robot system 1 may be applied to animals other than a human.

In addition to the above descriptions, the present inventive concept may be embodied in various forms.

As described above, according to the surgical robot system 1 and a method for controlling the surgical robot system 1 according to the one or more of the above embodiments of the present inventive concept, when an event occurs during an operation of the surgical robot system 1, information related to the event including a position where the event occurs may be quickly and accurately transmitted to the operator O or the assistant operator A.

Also, according to the surgical robot system 1 and a method for controlling the surgical robot system 1 according to the one or more of the above embodiments of the present inventive concept, when information about a cause of the event and a handling method thereof is provided with the information about a position where the event occurs, the operator O and the assistant operator A may be able to quickly take an action.

Thus, according to the one or more of the above embodiments of the present inventive concept, the event of the surgical robot system 1 may be quickly and accurately processed and thus a delay in a surgery time due to occurrence of an event or an error in handling the event, and generation of a medical accident according thereto may be effectively reduced.

I claim:

1. A surgical robot system comprising:
   a slave robot having a plurality of robot arms equipped with surgical tools;
   a master console performing remote control on the slave robot in response to a manipulation by an operator;
   a first display arranged around the slave robot; and
   a control portion outputting image information to the first display when an event occurs in the slave robot or the master console itself, wherein the image information includes information about a position where the event occurs on an image corresponding to a shape of the slave robot or the master console.

2. The surgical robot system of claim 1, wherein the control portion outputs text information related to the event to the first display with the image information.

3. The surgical robot system of claim 2, wherein the text information comprises at least one of information about a type of the event, a cause of the event, a method for handling the event, or a combination thereof.

4. The surgical robot system of claim 1, wherein the event comprises at least one of:
   initialization of the slave robot or the master console;
   completion of preparation for an operation of the slave robot or the master console;
   a communication error between the slave robot and the master console;
   an error in an actuator of the slave robot;
   an error in a signal of a sensor provided in the slave robot;
   an error in power of the slave robot;
   an error in mounting of the surgical tools;
   a replacement of the surgical tools;
   reaching an operational limit of the slave robot or an operation of an electric surgical tool mounted on the slave robot;
   separation of a head of the operator from the master console;
   an input of a preset instruction by the operator;
   an input of a preset instruction by an assistant operator;
   generation of manipulation to move a position of the slave robot; or
   a combination of thereof.

5. The surgical robot system of claim 1, further comprising a second display that is arranged on the master console, wherein the second display displays image information corresponding to an image displayed on the first display.

6. The surgical robot system of claim 1, wherein the event is generated according to an instruction of the operator, and the control portion receives an input of the information about the position of the event from the operator.

7. The surgical robot system of claim 1, wherein the first display is arranged on the master console, the event is generated according to an instruction of an assistant operator, and the control portion receives an input of the information about the position of the event from the assistant operator and outputs the image information to the first display.

8. The surgical robot system of claim 1, wherein the control portion further comprises a real-time robot image generation unit that generates in real time an image of the slave robot corresponding to a shape of the slave robot by using a sensor of the slave robot.

9. The surgical robot system of claim 1, wherein the first display is configured in the form of touch screen to receive an input from the operator.

10. A method for controlling a surgical robot system, the method comprising:
    generating an event in a slave robot or a master console itself of a surgical robot system, wherein the surgical robot system comprises the slave robot having a plurality of robot arms equipped with surgical tools, the master console performing remote control on the slave robot in response to a manipulation by an operator, and a first display arranged around the slave robot;
    generating image information including information about a position where the event occurs on an image corresponding to the slave robot or the master console; and
    outputting the image information to the first display.

11. The method of claim 10, wherein the image information further comprises text information related to the event.

12. The method of claim 11, wherein the text information comprises at least one of information about a type of the event, a cause of the event, a method for handling the event, or a combination thereof.

13. The method of claim 10, wherein the event comprises at least one of:
    initialization of the slave robot or the master console;
    completion of preparation for an operation of the slave robot or the master console;
    a communication error between the slave robot and the master console;
    an error in an actuator of the slave robot;
    an error in a signal of a sensor provided in the slave robot;
    an error in power of the slave robot;
    an error in mounting of the surgical tools;
    a replacement of the surgical tools;
    reaching an operational limit of the slave robot or an operation of an electric surgical tool mounted on the slave robot;
    separation of a head of the operator from the master console;
    an input of a preset instruction by the operator;
    an input of a preset instruction by an assistant operator;
    generation of manipulation to move a position of the slave robot; or
    a combination of thereof.

14. The method of claim 10, wherein the surgical robot system further comprises a second display that is arranged on the master console, and the second display displays image information corresponding to an image displayed on the first display.

15. The method of claim 10, wherein the event is generated according to an instruction of the operator, and the step of generating image information further comprises receiving an input of the information about the position of the event from the operator.

16. The method of claim 10, wherein the first display is arranged on the master console, the event is generated according to an instruction of an assistant operator, and the step of generating image information further comprises receiving an input of the information about the position of the event from the assistant operator.

17. The method of claim 10, further comprising generating in real time an image of the slave robot corresponding to a shape of the slave robot by using a sensor of the slave robot.

18. The method of claim 10, wherein the first display is configured in the form of touch screen to receive an input from the operator.

* * * * *